(12) United States Patent
Laviano et al.

(10) Patent No.: US 10,070,874 B2
(45) Date of Patent: Sep. 11, 2018

(54) METHODS OF FIXATING TISSUE TO BONE

(71) Applicant: Arthrex, Inc., Naples, FL (US)

(72) Inventors: Anthony A. Laviano, Fort Myers, FL (US); Jacob A. Jolly, Naples, FL (US); Kenneth T. Helenbolt, Naples, FL (US); Augusto Custodio, Naples, FL (US)

(73) Assignee: Arthrex, Inc., Naples, FL (US)

( * ) Notice: Subject to any disclaimer, the term of this patent is extended or adjusted under 35 U.S.C. 154(b) by 216 days.

(21) Appl. No.: 15/240,804

(22) Filed: Aug. 18, 2016

(65) Prior Publication Data
US 2018/0049755 A1    Feb. 22, 2018

(51) Int. Cl.
*A61B 17/17*    (2006.01)
*A61B 17/16*    (2006.01)
*A61F 2/08*    (2006.01)

(52) U.S. Cl.
CPC ...... *A61B 17/1714* (2013.01); *A61B 17/1615* (2013.01); *A61B 17/1675* (2013.01); *A61B 17/1764* (2013.01); *A61F 2/0811* (2013.01); *A61F 2002/0882* (2013.01)

(58) Field of Classification Search
CPC ............... A61B 17/1714; A61B 17/1615
See application file for complete search history.

(56) References Cited

U.S. PATENT DOCUMENTS

| | | | |
|---|---|---|---|
| 8,882,833 B2 | 11/2014 | Saylor et al. | |
| 9,138,223 B2 | 9/2015 | Jolly et al. | |
| 9,549,769 B2 | 1/2017 | LeBeau et al. | |
| 2001/0018588 A1 | 8/2001 | Harder et al. | |
| 2001/0053934 A1* | 12/2001 | Schmieding | A61B 17/1714 623/13.14 |
| 2003/0065391 A1* | 4/2003 | Re | A61B 17/1714 623/13.14 |
| 2004/0199166 A1* | 10/2004 | Schmieding | A61B 17/1617 606/79 |
| 2007/0093840 A1 | 4/2007 | Pacelli et al. | |
| 2007/0276395 A1 | 11/2007 | Burn | |
| 2008/0188935 A1 | 8/2008 | Saylor | |
| 2009/0326538 A1 | 12/2009 | Sennett et al. | |
| 2010/0217315 A1* | 8/2010 | Jolly | A61B 17/06 606/223 |
| 2010/0268234 A1 | 10/2010 | Aho et al. | |
| 2011/0208194 A1 | 8/2011 | Steiner et al. | |
| 2012/0041485 A1 | 2/2012 | Kaiser et al. | |
| 2012/0041486 A1 | 2/2012 | Stone et al. | |
| 2012/0191095 A1 | 7/2012 | Burger et al. | |
| 2012/0265205 A1 | 10/2012 | Steiner et al. | |

(Continued)

FOREIGN PATENT DOCUMENTS

WO    2016025705 A1    2/2016

OTHER PUBLICATIONS

International Search Report and Written Opinion for corresponding PCT Application No. PCT/2017/046477 dated Dec. 4, 2017.

*Primary Examiner* — Christian Sevilla
(74) *Attorney, Agent, or Firm* — McDonnell Boehnen Hulbert & Berghoff LLP

(57) ABSTRACT

A drill pin and a method of fixating tissue to bone is described herein. A method of fixating tissue to a bone with a fixation button is described that includes advancing a drill pin from a first surface of a bone to a second surface of the bone to form a tunnel.

21 Claims, 11 Drawing Sheets

(56) References Cited

U.S. PATENT DOCUMENTS

2013/0090658 A1  4/2013 Kam
2013/0261628 A1  10/2013 Burley et al.
2015/0127012 A1  5/2015 Pilgeram
2015/0133941 A1  5/2015 Saylor et al.

\* cited by examiner

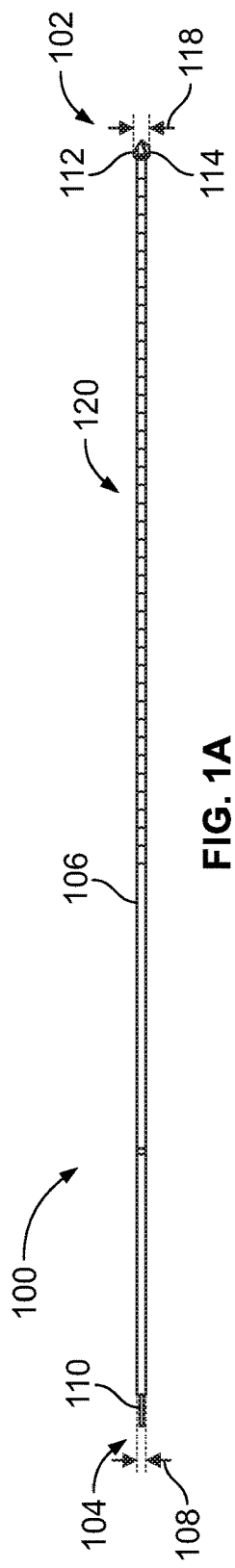
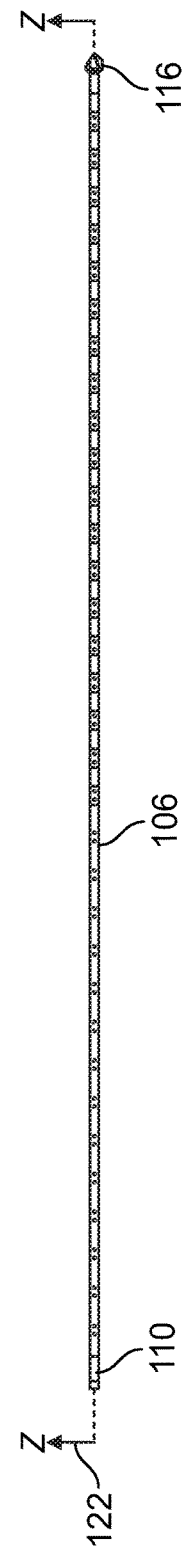
FIG. 1A
FIG. 1B

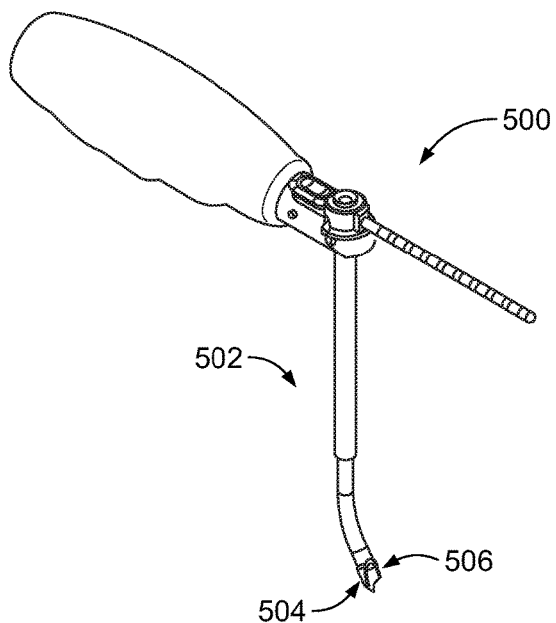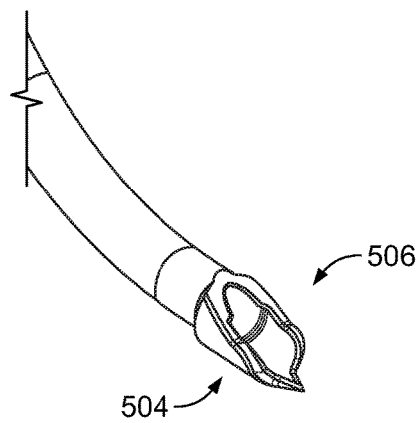
FIG. 16A  FIG. 16B
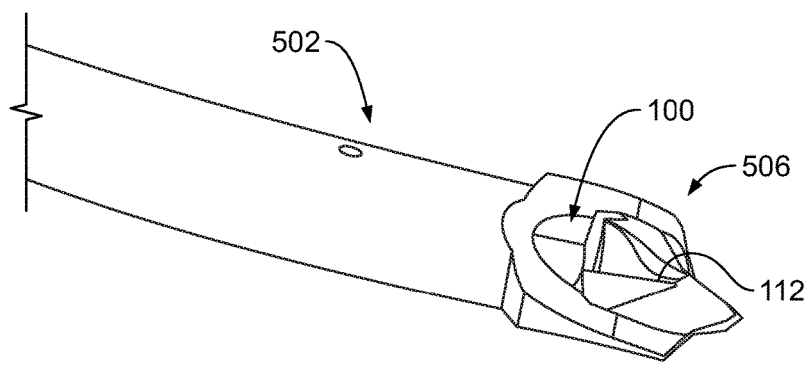
FIG. 17

METHODS OF FIXATING TISSUE TO BONE

BACKGROUND

The present disclosure generally relates to surgical procedures and, more particularly, to methods and systems for ligament repair and reconstruction with suture and/or graft passage.

A typical ligament repair and reconstruction operation involves drilling a tunnel through a bone using a guide pin (also referred to herein as a "drill pin") having a suture-passing mechanism. The guide pin can be used as a guide for a cannulated reamer that can be placed over the guide pin to drill a graft socket in the bone. The ligament repair and reconstruction operation can also involve implanting a suspensory fixation button to facilitate graft attachment to the bone. Fixation buttons can be used for fixation of bone to bone or soft tissue to bone, and the buttons are intended as fixation posts, a distribution bridge, or for distributing suture tension over areas of ligament or tendon repair. In an example, the ligament repair and reconstruction operation is an anterior cruciate ligament (ACL) and/or posterior cruciate ligament (PCL) repair and reconstruction.

SUMMARY

In typical ligament repair and reconstruction operations, the ligament repair and reconstruction operation involves the guide pin pulling the fixation button through the area drilled by the guide pin and pulling the graft into the graft socket. However, the fixation button typically has a width larger in size than the diameter of the tunnel formed by the guide pin, in order to provide a large enough footprint for acting as a fixation post, a distribution bridge, or for distributing suture tension over areas of ligament or tendon repair. For instance, fixation buttons commonly used during ligament repair and reconstruction operations have a width of 3.4 millimeters (mm) or higher. As a particular example, Arthrex Inc. of Naples, Fla. provides a TightRope® Attachable Button System (ABS) having a fixation button with a 3.4 mm width and an 11 mm length. As another example, Arthrex Inc. provides a TightRope® ABS Oblong button having a 3.4 mm width and a 13 mm length. In order to install these fixation buttons that have a width of 3.4 mm or higher, surgeons typically drill a 4 mm or larger tunnel. However, existing guide pins for ligament repair and reconstruction operations form tunnels substantially less than 4 mm in diameter. Since existing guide pins for ligament repair and reconstruction operations form tunnels less than 4 mm in diameter, a surgeon typically needs to over drill the guide pin as a second step to accommodate the larger size of the fixation button.

The ligament repair and reconstruction operation can also involve measurement of tunnel depth during the operation. This measured tunnel depth can be used when determining the size of and drilling the graft socket. Typically, in order to measure tunnel depth, the guide pin is removed from the drilled tunnel, and then a separate measurement instrument is inserted in order to measure tunnel depth. Alternatively, existing guide pins can have markings along the drill pin to facilitate measurement of tunnel depth during the operation. However, it is difficult for a surgeon to precisely align existing guide pins with the opening of the tunnel in order to obtain a precise measurement of the tunnel depth.

The methods and systems in accordance with the present disclosure beneficially provide improved methods and systems for fixating tissue to a bone with a fixation button. The disclosed methods and systems eliminate the step of over drilling the guide pin as a second step to accommodate the larger size of the fixation button. Further, in accordance with example embodiments, the disclosed methods and systems also provide improved methods and systems that allow for precisely aligning the drill pin with the opening of the tunnel in order to obtain a precise measurement of the tunnel depth.

In an example in accordance with the present disclosure, a method of fixating tissue to bone with a fixation button is described. The method includes advancing a drill pin from a first surface of a bone to a second surface of the bone to form a tunnel. The drill pin includes (a) a flexible shaft having a first outer diameter, (b) an eyelet for suture passing located on the flexible shaft, (c) an oversized drill tip located at a distal end of the flexible shaft and comprising at least one flute, wherein the oversized drill tip has a second outer diameter that is at least 1.5 times the first outer diameter, and (d) markings along the flexible shaft to allow measurement of a distance from the oversized drill tip. The method can further include positioning the oversized drill tip against the second surface of the bone and determining a depth of the tunnel based on the markings along the flexible shaft. The method can also include advancing a cannulated reamer over the flexible shaft of the drill pin to form a tissue socket having a diameter greater than the second outer diameter and a length less than the determined tunnel depth and attaching a fixation button and tissue to the drill pin using passing sutures attached to the eyelet. The fixation button has a width that is greater than the first outer diameter of the flexible shaft but less than the second outer diameter of the oversized drill tip. The method then includes advancing the eyelet through the tunnel and tissue socket, so as to move the fixation button through the tunnel and to move the tissue into the socket, and fixating the tissue to the socket with the fixation button.

In another example in accordance with the present disclosure, a method of fixating a tissue to bone with a fixation button is described. The method includes advancing a drill pin from a first surface of a bone to a second surface of the bone to form a tunnel. The drill pin includes (a) a shaft having a proximal end and a distal end, wherein the shaft has a first outer diameter of approximately 2.4 mm, (b) an eyelet for suture passing located at the proximal end of the shaft, and (c) an oversized drill tip located at the distal end of the shaft and comprising at least one flute, wherein the oversized drill tip has a second outer diameter of approximately 4 mm or higher. The method also includes advancing a cannulated reamer over the shaft of the drill pin to form a tissue socket and attaching a fixation button and tissue to the drill pin using passing sutures attached to the eyelet, wherein the fixation button has a width that is approximately 3.4 mm or higher. The method then includes advancing the eyelet through the tunnel and tissue socket, so as to move the fixation button through the tunnel and to move the tissue into the socket, and fixating the tissue to the bone with the fixation button.

In another example in accordance with the present disclosure, a method of fixating a tissue to bone with a fixation button is described. The method includes advancing a drill pin from a first surface of a bone to a second surface of the bone to form a tunnel. The drill pin includes (a) a flexible shaft having a first outer diameter, (b) an eyelet for suture passing located on the flexible shaft, (c) an oversized drill tip located at a distal end of the flexible shaft and comprising at least one flute, wherein the oversized drill tip has a second outer diameter that is at least about 1.25 to about 1.75 times the first outer diameter, and (d) markings along the flexible shaft to allow measurement of a distance from the oversized drill tip. The method can further include positioning the oversized drill tip against the second surface of the bone and determining a depth of the tunnel based on the markings along the flexible shaft. The method can also include advancing a cannulated reamer over the flexible shaft of the drill pin to form a tissue socket having a diameter greater than the second outer diameter and a length less than the determined tunnel depth and attaching a fixation button and tissue to the drill pin using passing sutures attached to the eyelet. The fixation button has a width that is greater than the first outer diameter of the flexible shaft but less than the second outer diameter of the oversized drill tip. The method can also include advancing the eyelet through the tunnel and tissue socket, so as to move the fixation button through the tunnel and to move the tissue into the socket, and fixating the tissue to the socket with the fixation button.

The features, functions, and advantages that have been discussed can be achieved independently in various embodiments or may be combined in yet other embodiments further details of which can be seen with reference to the following description and drawings.

BRIEF DESCRIPTION OF THE FIGURES

FIGS. 1a-b illustrate side views of an example drill pin, according to an example embodiment.

FIG. 16a illustrates an example curved guide that can be used with the example drill pin of FIG. 1, according to an example embodiment.

FIG. 16b illustrates a close-up view of a tip of the curved guide of FIG. 16a, according to an example embodiment.

FIG. 17 illustrates a perspective view of the drill pin of FIG. 1 in the curved guide of FIG. 16a, according to an example embodiment.

DETAILED DESCRIPTION

Figure 2A:
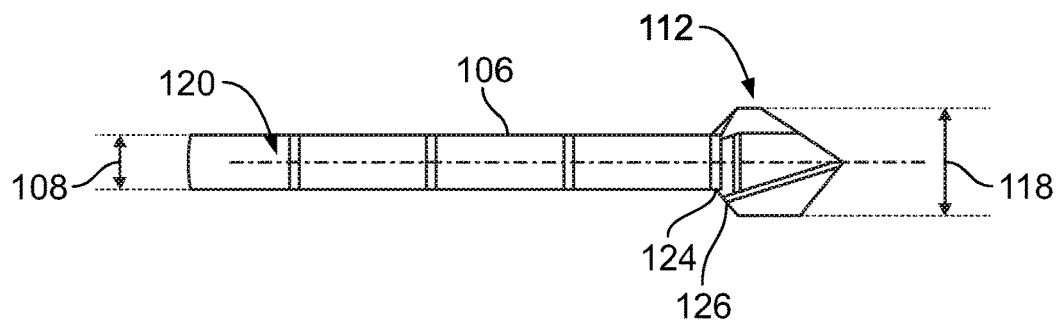
FIG. 2a illustrates a side view of the oversized drill tip of the drill pin of FIG. 1, according to an example embodiment.

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein.

As described above, existing guide pins for ligament repair and reconstruction operations form tunnels substantially less than 4 mm in diameter. Since existing guide pins for ligament repair and reconstruction operation form tunnels substantially less than 4 mm in diameter, a surgeon typically needs to over drill the guide pin as a second surgical step to accommodate the larger size of the fixation button. Further, it is difficult for a surgeon to precisely align existing guide pins with the opening of the tunnel in order to obtain a precise measurement of the tunnel depth.

The methods and systems in accordance with the present disclosure beneficially provide improved methods and systems for fixating tissue to a bone with a fixation button that eliminate the step of over drilling the guide pin as a second step to accommodate the larger size of the fixation button. The disclosed methods and systems also provide improved methods and systems that allow for precisely aligning the drill pin with the opening of the tunnel in order to obtain a precise measurement of the tunnel depth.

In one example, a method of fixating tissue to a bone with a fixation button is described. The method includes advancing a drill pin from a first surface of a bone to a second surface of the bone to form a tunnel. The drill pin includes (a) a flexible shaft having a first outer diameter, (b) an eyelet for suture passing located on the flexible shaft, (c) an oversized drill tip located at a distal end of the flexible shaft and comprising at least one flute, wherein the oversized drill tip has a second outer diameter that is at least 1.5 times the first outer diameter, and (d) markings along the flexible shaft to allow measurement of a distance from the oversized drill tip. An embodiment of the method further includes positioning the oversized drill tip against the second surface of the bone and determining a depth of the tunnel based on the markings along the flexible shaft. An embodiment of the method also includes advancing a cannulated reamer over the flexible shaft of the drill pin to form a tissue socket having a diameter greater than the second outer diameter and a length less than the determined tunnel depth. An embodiment of the method also includes attaching a fixation button and tissue to the drill pin using passing sutures attached to the eyelet. An embodiment of the fixation button has a width that is greater than the first outer diameter of the flexible shaft but less than the second outer diameter of the oversized drill tip. An embodiment of the method then includes advancing the eyelet through the tunnel and tissue socket, so as to move the fixation button through the tunnel and to move the tissue into the socket, and then fixating the tissue to the socket with the fixation button.

An oversized drill tip located at a distal end of the flexible shaft and comprises at least one flute. The term "oversized" refers to the drill tip having a second outer diameter that is larger than a first outer diameter. In an embodiment, the second outer diameter is at least about 1.1, about 1.2, about 1.25, about 1.3, about 1.4, about 1.5, about 1.6, about 1.7, about 1.75, about 1.8, about 1.9, and about 2 times larger than the first outer diameter. In an embodiment, the second outer diameter is about 1.1 to about 2, about 1.2 to about 2, about 1.25 to about 2, about 1.3 to about 2, about 1.4 to about 2, about 1.5 to about 2, about 1.6 to about 2, about 1.7 to 2, about 1.75 to about 2, about 1.25 to about 1.75, about 1.3 to about 1.75, about 1.4 to about 1.75, about 1.5 to about 1.75, about 1.25 to about 1.7, about 1.3 to about 1.7, about 1.4 to about 1.7, about 1.5 to about 1.7, about 1.25 to about 1.6, about 1.3 to about 1.6, about 1.4 to about 1.6, about 1.5 to about 1.6 times, about 1.25 to about 1.5, about 1.3 to about 1.5, about 1.4 to about 1.5, about 1.5 to about 1.8, about 1.5 to about 1.9, about 1.4 to about 1.6, about 1.4 to about 1.8, or about 1.4 to about 1.9 times larger than the first outer diameter. In an embodiment, an oversized drill tip comprises a) a first outer diameter of about 1.5 mm, about 1.75 mm, about 2 mm, about 2.1 mm, about 2.2 mm, about 2.25 mm, about 2.3 mm, about 2.4 mm, about 2.5 mm, about 2.6 mm, about 2.7 mm, about 2.75 mm, about 2.8 mm, about 2.9 mm, or about 3 mm; and b) a second outer diameter of about 2.7 mm, about 2.8 mm, about 2.9 mm, about 3 mm, about 3.25 mm, about 3.5 mm, about 3.75 mm, about 4 mm, about 4.5 mm, or about 5 mm. In an embodiment, the second outer diameter is of a size to allow passage of a fixation device without overdrilling. The term "overdrilling" refers to increasing the size of a bone tunnel by drilling with a cannulated reamer over a drill pin.

Referring now to FIGS. 1*a-b*, an example drill pin 100 for drilling a tunnel through a bone and for suture passing is illustrated. FIG. 1*a* illustrates a first side view of the drill pin 100, and FIG. 1*b* illustrates a second side view of the drill pin 100 where the drill pin is rotated about 90 degrees from the orientation shown in FIG. 1*a*.

The drill pin 100 has a distal end 102 and a proximal end 104. Drill pin 100 includes a flexible shaft 106 having a first outer width or diameter 108. The drill pin 100 also includes an eyelet 110 for suture passing located on the flexible shaft 106. The drill pin 100 further includes an oversized drill tip 112 located at a distal end 114 of the flexible shaft 106. The oversized drill tip 112 includes at least one flute 116 (see FIG. 1*b*), and the oversized drill tip 112 has a second outer width or diameter 118 (see FIG. 1*a*). In an example, the drill pin 100 is an un-cannulated drill pin.

In an example embodiment, the width of the oversized drill tip 112 is substantially larger than the width of the flexible shaft 106. In particular, second outer diameter 118 is substantially larger than the first outer diameter 108. As used herein, a given diameter is substantially larger than another diameter when the given diameter is at least 1.5 times the other diameter. Therefore, in an example embodiment, the second outer diameter 118 is at least 1.5 times the first outer diameter 108. In a particular example, the first outer diameter 108 is approximately 2.4 mm and the second outer diameter 118 is approximately 4 mm. In another example embodiment, the width of the oversized drill tip 112 is at least 1.25 times the first outer diameter 108. In a particular example, the first outer diameter 108 is approximately 2.7 mm and the second outer diameter 118 is approximately 4 mm.

The drill pin 100 also includes markings 120 along the flexible shaft 106 to allow measurement of a distance from the oversized drill tip 112. In an example, the markings 120 are laser markings along the flexible shaft 106 that identify mm between 1-20 mm along the flexible shaft 106. However, in other examples, different measurement scales and more or fewer markings are possible. For instance, in another example, the markings 120 also identify half mm. Other examples are possible as well.

The eyelet 110 can be any suitable eyelet for passing sutures (e.g., flexible strands) or passing members from a fixation button. In the example shown in FIGS. 1*a-b*, the eyelet 110 is a slot formed integral with the flexible shaft 106. However, in another example, the eyelet 110 comprises a wire loop crimped to the proximal end 104 of the drill pin 100.

Figure 2B:
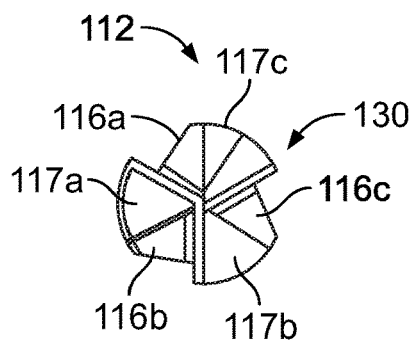
FIG. 2b illustrates a top view of the oversized drill tip of the drill pin of FIG. 1, according to an example embodiment.

In an example, oversized drill tip 112 is a substantially cylindrical drill tip comprising a cutting edge having three flats spaced approximately 120 degrees apart with flutes. FIG. 2*a* illustrates a side view of the oversized drill tip 112 and FIG. 2*b* illustrates a top view of the oversized drill tip 112. As seen in FIGS. 2*a-b*, the oversized drill head 112 has a substantially cylindrical profile 130 with three flutes 116*a-c* cut out of the substantially cylindrical profile 130. The centers of the flats 117*a-c* are spaced approximately 120 degrees apart from one another, as seen in FIG. 2*b*. The flutes 116*a-c* allow for drilled material (e.g., bone or tissue) to move back into the tunnel during the drilling process. Further, the substantially cylindrical profile 130 with flutes 116*a-c* allow the second outer diameter 118 of the oversized drill tip 112 to be substantially larger than the first outer diameter 108 of the flexible shaft 106 to which the oversized drill tip 112 is attached. Although the example in FIGS. 2*a-b* includes three flats and three flutes, more or fewer flats and flutes are possible as well.

In an example, the flexible shaft 106 and oversized drill tip 112 are formed from nitinol. However, other flexible materials are possible as well, including but not limited to wound wire, plastic, carbon fiber, and flexible laser cut stainless steel. In another example, the drill pin 100 is non-flexible rather than flexible. For example, drill pin 100 can be formed from non-flexible material, including but not limited to stainless steel or stainless steel tubing. Further, in an example, the shaft 106 and the drill tip 112 are formed from different materials. For instance, the shaft 106 can be formed from flexible material and the oversized drill tip 112 can be formed from non-flexible material. In an example, the flexible shaft 106 is made from different flexible materials while the oversized drill tip 112 is made from a noncorrosive metal.

Figure 3:
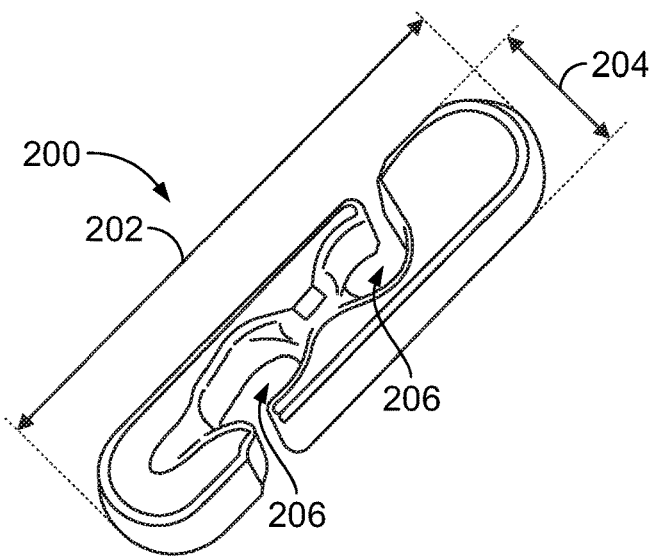
FIGS. 3-4 illustrate example fixation buttons, according to an example embodiment.

Drill pin 100 can be used with fixation buttons during ligament repair and reconstruction procedures, such as ACL and/or PCL repair and reconstruction. FIG. 3 illustrates an example fixation button 200 for ligament repair and reconstruction operations. Fixation button 200 has an oblong configuration such that the length 202 of the fixation button 200 is substantially greater than the width 204 of the fixation button 200. In an example, the length 202 of the fixation button 200 is at least 10 mm and the width 204 of the fixation button is at least approximately 3.4 mm. The button 200 includes at least one eyelet 206 that allows for passage of a flexible strand such as the passing suture. FIG. 3 depicts two eyelets 206; however, more or fewer eyelets are possible. In an example embodiment, the length 202 of the button is between approximately 10 mm and 20 mm and the width 204 is between approximately 3.4 and 4 mm.

Figure 4:
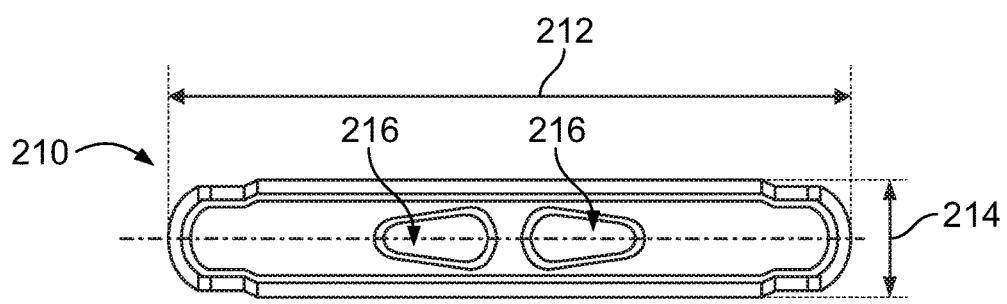

FIG. 4 illustrates another example fixation button 210 or ligament repair and reconstruction operations. Similar to fixation button 200, fixation button 210 has an oblong configuration such that the length 212 of the fixation button 210 is substantially greater than the width 214 of the fixation button 210. In an example, the length 212 of the fixation button 210 is at least 10 mm and the width 214 of the fixation button is at least 3.4 mm. The button 210 includes at least one eyelet 216 that allows for passage of a flexible strand such as the passing suture. FIG. 4 depicts two eyelets 216; however, more or fewer eyelets are possible. In a particular example, the fixation button is the oblong TightRope® ABS Button (AR-1588 TB-2), measuring 3.4 mm×13 mm, provided by Arthrex, Inc. of Naples, Fla. However, other fixation buttons are possible as well.

In order to install such fixation buttons 200, 210 having a width 3.4 mm or higher using existing drill pins, it is necessary to over drill the tunnel formed by the drill pin as a second operation, so as to create a tunnel large enough to accommodate the fixation buttons 200, 210. Beneficially, the disclosed methods and systems can be used to drill a tunnel having a size large enough to install fixation buttons such as fixation buttons 200, 210 without over drilling the tunnel. Therefore, the disclosed methods and systems beneficially provide a less complex and more efficient method for fixating tissue to bone with a fixation button.

Figure 5:
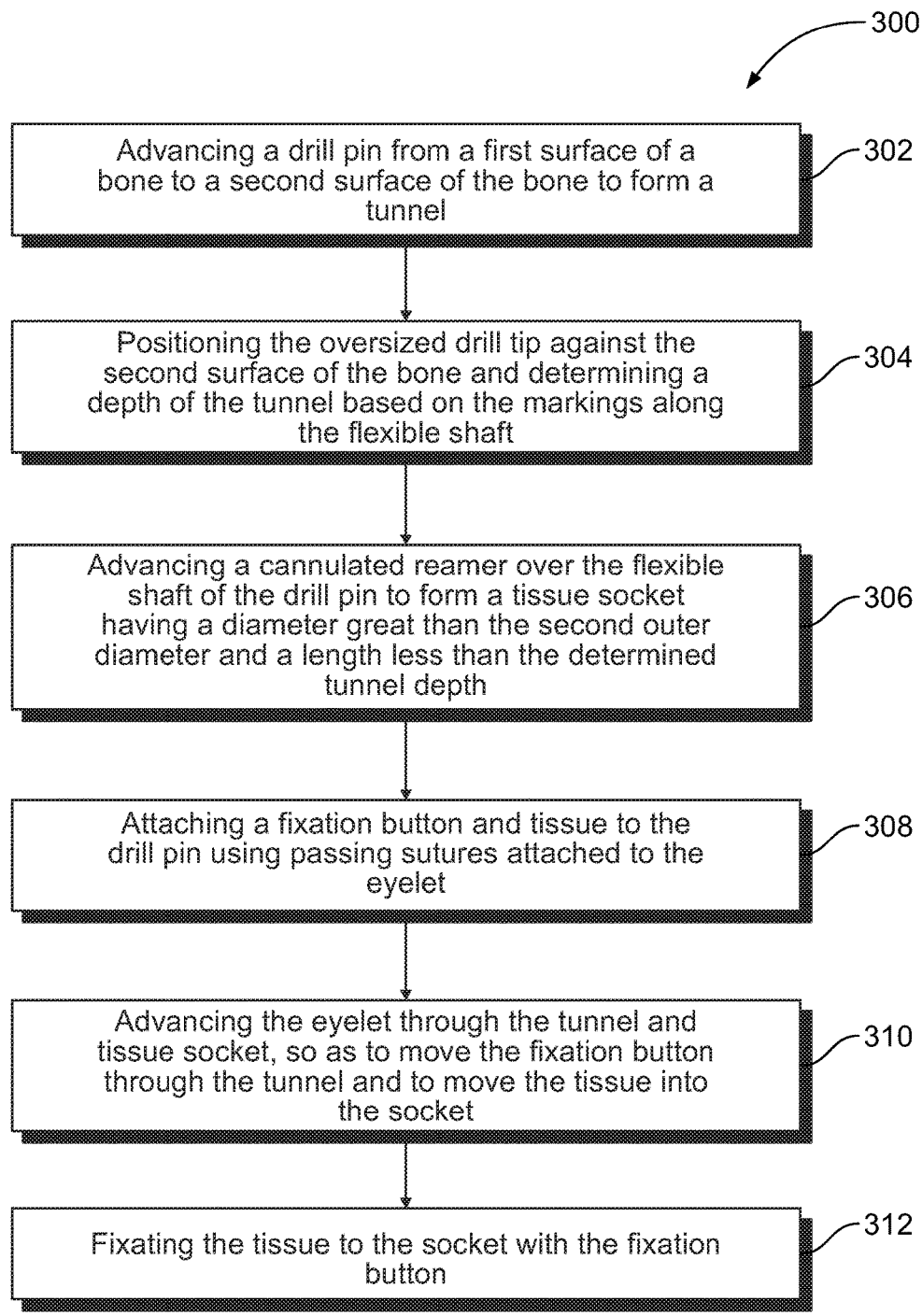
FIG. 5 shows a flowchart of an example method for fixating tissue to a bone with a fixation button, according to an example embodiment.

FIG. 5 shows a flowchart of an example method 300 for fixating tissue to a bone with a fixation button, according to an example embodiment. Method 300 shown in FIG. 5 presents an embodiment of a method that, for example, could be used with the drill pin 100 and fixation button 200 or 210 shown in FIGS. 1a-4, for example. It should be understood that for this and other processes and methods disclosed herein, the flowchart shows functionality and operation of one possible implementation of present embodiments. Alternative implementations are included within the scope of the example embodiments of the present disclosure in which functions can be executed out of order from that shown or discussed, including substantially concurrent or in reverse order, depending on the functionality involved, as would be understood by those reasonably skilled in the art.

As shown in FIG. 5, at block 302, the example method 300 involves advancing a drill pin from a first surface of a bone to a second surface of the bone to form a tunnel. The example method then involves, at block 304, positioning the oversized drill tip against the second surface of the bone and determining a depth of the tunnel based on the markings along the flexible shaft. Further, the example method involves, at block 306, advancing a cannulated reamer over the flexible shaft of the drill pin to form a tissue socket having a diameter greater than the second outer diameter and a length less than the determined tunnel depth. Still further, the example method involves, at block 308, attaching a fixation button and tissue to the drill pin using passing sutures attached to the eyelet, wherein the fixation button has a width that is greater or substantially greater than the first outer diameter of the flexible shaft but less than the second outer diameter of the oversized drill tip. Yet still further, the method involves, at block 310, advancing the eyelet through the tunnel and tissue socket, so as to move the fixation button through the tunnel and to move the tissue into the socket. And yet still further, the method involves, at block 312, fixating the tissue to the socket with the fixation button. In an example embodiment, method 300 is carried out during an ACL and/or PCL reconstruction. However, other example operations in which method 300 can be carried out are possible as well.

Figure 6:
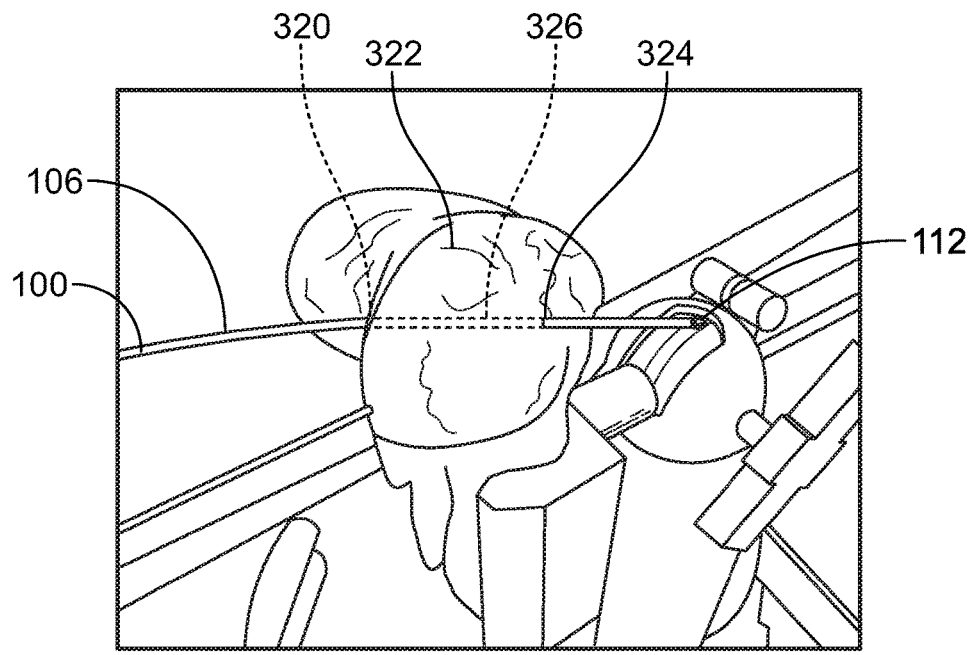
FIGS. 6-14 illustrate various steps of the example method of FIG. 5 for fixating tissue to a bone with a fixation button, according to an example embodiment.

Example method 300 is described in further detail with reference to FIGS. 6-14. As seen in FIG. 6, example method 300 involves advancing drill pin 100 from a first surface 320 of a bone 322 to a second surface 324 of the bone 322 to form a tunnel 326. Due to the oversized drill tip 112, the tunnel 326 has a diameter that is substantially greater than the diameter 108 of the flexible shaft 106, in order to accommodate the fixation button 200 or 210. In a particular example, the diameter of the tunnel 326 is at least approximately 4 mm and the diameter 108 of the flexible shaft 108 is 2.4 mm.

Figure 7:
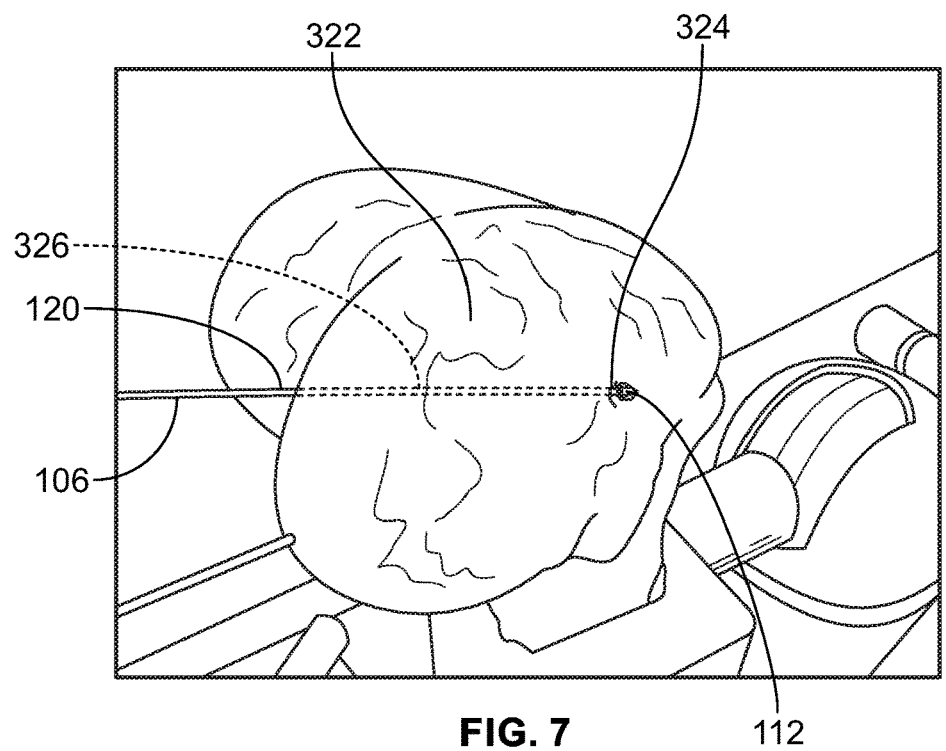

The example method also involves, at block 304, positioning the oversized drill tip 112 against the second surface 324 of the bone and determining a depth of the tunnel 326 based on the markings 120 along the flexible shaft 106. The drill pin 100 is configured so that the oversized drill tip 112 can act as a positive stop during the measurement, which beneficially helps a surgeon to both quickly and precisely measure depth of tunnel 326. As seen in FIG. 1b, the flexible shaft 106 includes a longitudinal axis 122. Further, a proximal end 124 (see FIG. 2a) of the oversized drill tip 112 comprises a proximal surface 126 that is substantially perpendicular to the longitudinal axis 122 of the flexible shaft 106. This substantially-perpendicular proximal surface 126 can act as a positive stop to facilitate measurement of the depth of the tunnel 326 formed by drill pin 100. In an example embodiment, positioning the oversized drill tip 112 against the second surface 324 of the bone 322 comprises positioning the substantially-perpendicular proximal surface 126 against the second surface 324 of the bone 322. For instance, FIG. 7 illustrates the substantially-perpendicular proximal surface 126 positioned against the second surface 324 of bone 322.

In an example embodiment, the proximal surface of the oversized drill tip 112 has a width or diameter that is substantially greater than the diameter of the flexible shaft 106. For example, the diameter of the proximal surface can be approximately 4 mm or higher, and the diameter of the flexible shaft can be approximately 2.4 mm. Further, in an example embodiment, the proximal surface that is substantially perpendicular to the longitudinal axis of the flexible shaft extends at an angle between 75 and 105 degrees from the longitudinal axis of the flexible shaft. In another example embodiment, the flexible shaft extends at an angle between 80 and 100 degrees from the longitudinal axis of the flexible shaft. In yet another example embodiment, the flexible shaft extends at an angle between 85 and 95 degrees from the longitudinal axis of the flexible shaft. Such a substantially perpendicular angle allows the oversized drill tip 112 to act as a positive stop against the bone 322 and having such a positive stop can help to obtain a precise measurement of the tunnel depth.

In an example embodiment of method 300, step 304 is an optional step. For instance, in some example operations, step 304 can be omitted.

Figure 8:
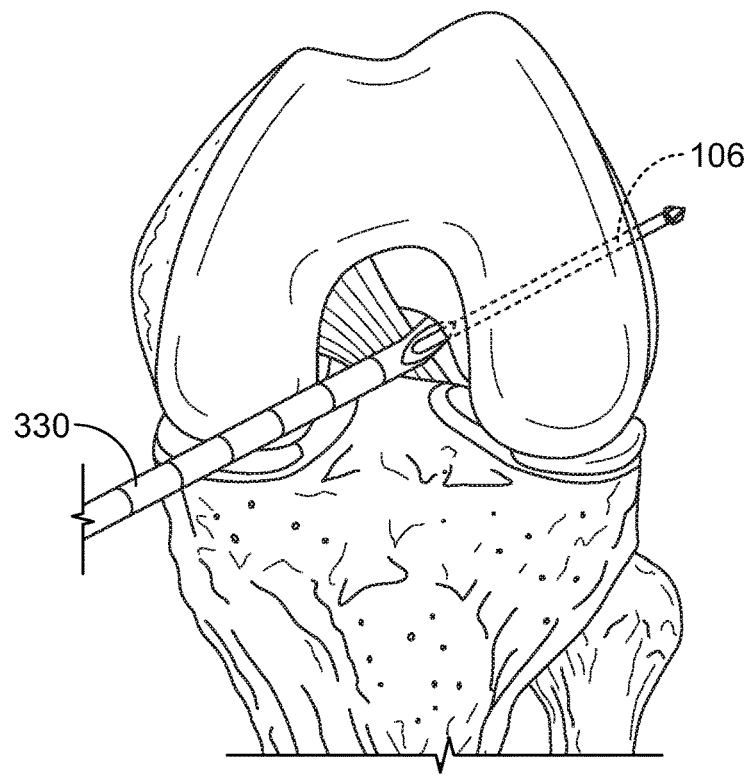
Figure 9:
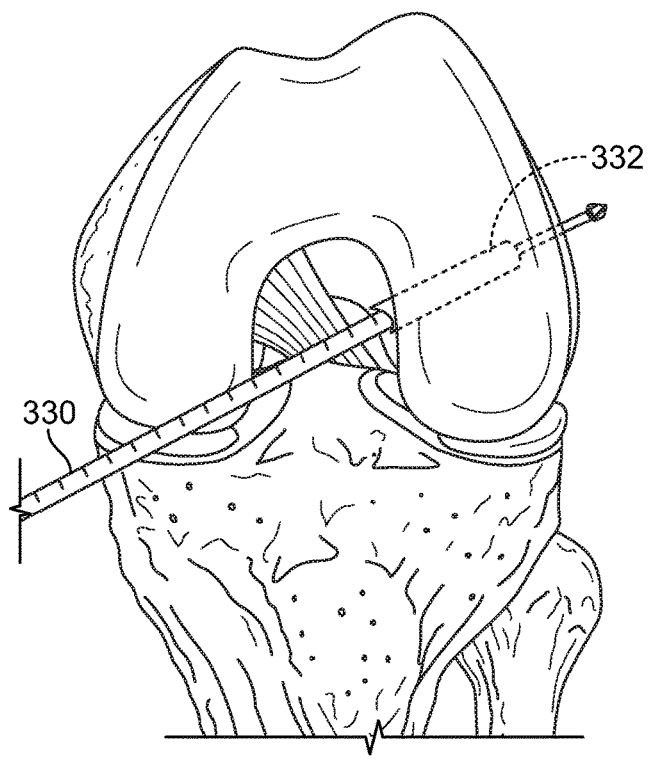

With reference to FIGS. 8 and 9, the method involves, at block 306, advancing a cannulated reamer 330 over the flexible shaft 106 of the drill pin 100 to form a tissue socket 332 (see FIG. 9) having a diameter greater than the second outer diameter 118 and a length less than the determined tunnel depth. Cannulated reamer 330 can be a cannulated reamer that is configured to drill over a 2.4 mm guide pin. Further, in an example, the diameter of the tissue socket 332 is between 5-8 mm, the length of the tissue socket is approximately 20 mm or higher, and the determined tunnel depth is approximately 30 mm or higher. Other example measurements are possible as well.

Figure 10:
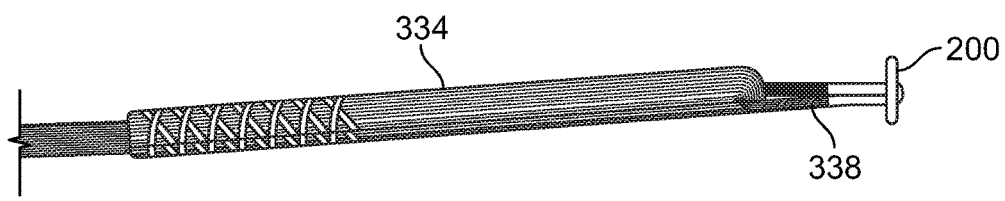
Figure 11:
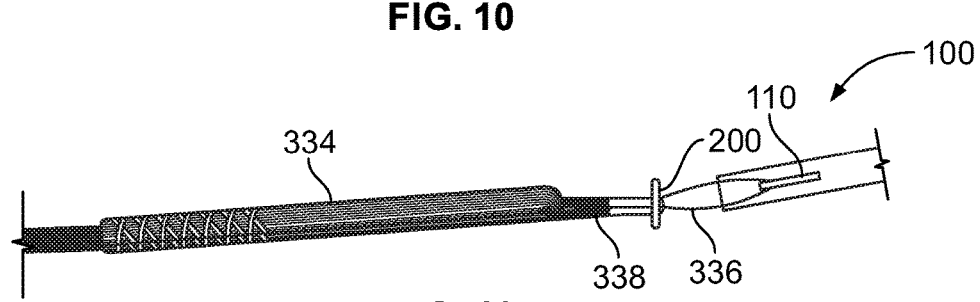

The tissue socket 332 can be used for positioning tissue during the operation, and the tunnel 326 can be used in order to pass the fixation button and passing sutures beyond the second side 324 of the bone 322. With reference to FIGS. 10-11, the method also involves, at block 308, attaching fixation button 200 and tissue 334 to the drill pin 100 using passing sutures 336 attached to the eyelet 110. In an example, the tissue 334 is a graft, a ligament, or a tendon. In an example, the graft includes a ligament and/or a tendon. In another example, the tissue 334 is synthetic tissue.

In an example embodiment, attaching fixation button 200 and tissue 334 to the drill pin 100 using passing sutures 336 attached to the eyelet 110 involves attaching the fixation button 200 and the tissue 334 with sutures 338 and attaching passing sutures 336 (see FIG. 11) to the fixation button 200. After attaching passing sutures 336 to the fixation button 200, the passing sutures 336 are then secured to the eyelet 110 (see FIG. 11).

The step of attaching the fixation button 200 and tissue 334 to the drill pin 100 using passing sutures 336 attached to the eyelet 110 can be performed at any suitable time. In an example, this step is performed after the cannulated reamer 330 forms the tissue socket 332. Further, in an example, these steps are both performed without removing the drill pin 100 from the tunnel 326. Beneficially, by avoiding removing the drill pin 100 from the tunnel 326, the overall operation time can be reduced. However, in another example, the drill pin 100 can be removed from the tunnel 326 in order to attach the fixation button 200 and tissue 334 to the drill pin 100. After the fixation button 200 and tissue 334 are attached to the drill pin 100, drill pin 100 can then be reinserted into the tunnel 326.

Figure 12:
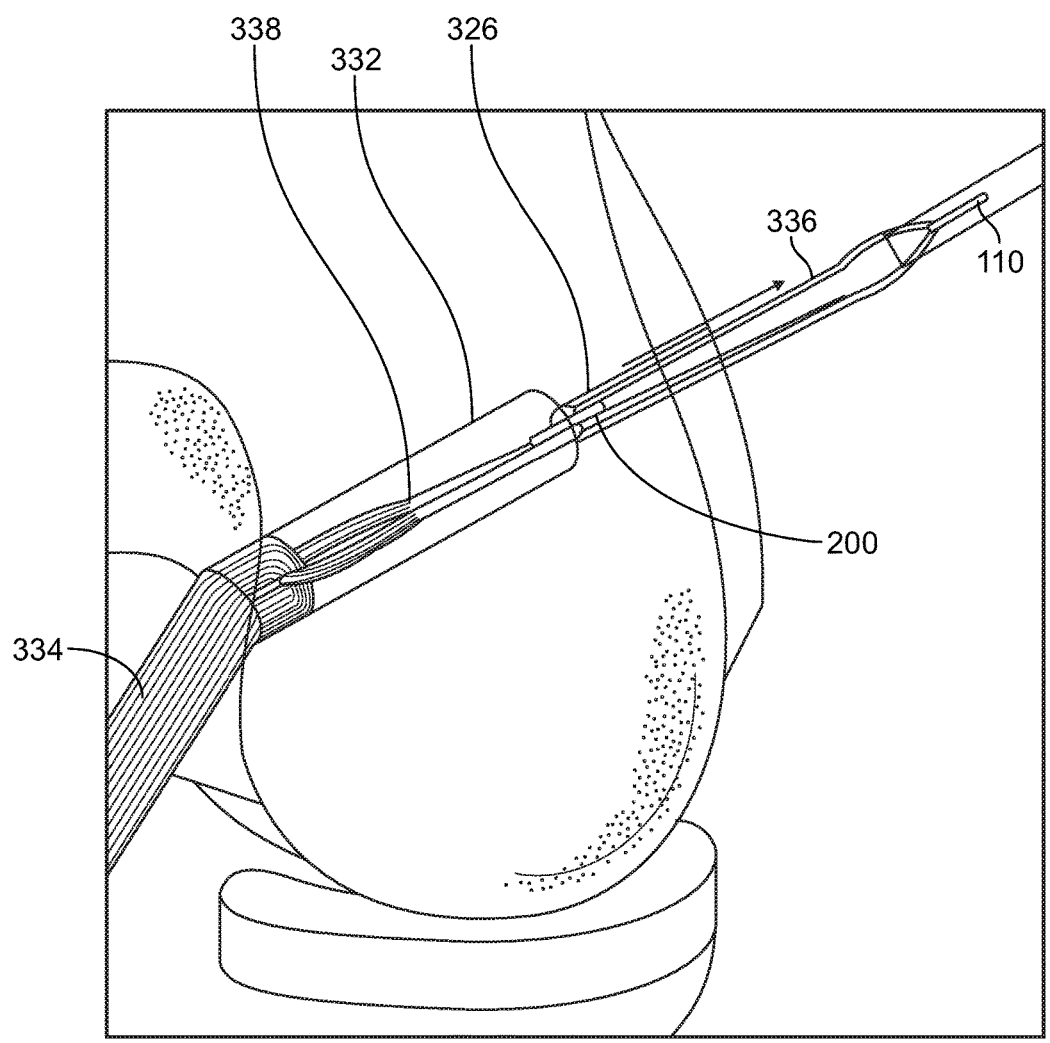

With reference to FIG. 12, the method then involves, at block 310, advancing the eyelet 110 of the drill pin 100 through the tunnel 326 and tissue socket 332, so as to move the fixation button 200 through the tunnel 326 and to move the tissue into the tissue socket 332. As mentioned above, the tunnel 326 is at least 4 mm and the fixation button 200 has a width that is greater than the first outer diameter 108 of the flexible shaft 106 but less than the second outer diameter 118 of the oversized drill tip 112. Therefore, the fixation button 200 can be moved through the tunnel 326 formed by drill pin 100 without over drilling of the tunnel 326.

Figure 13:
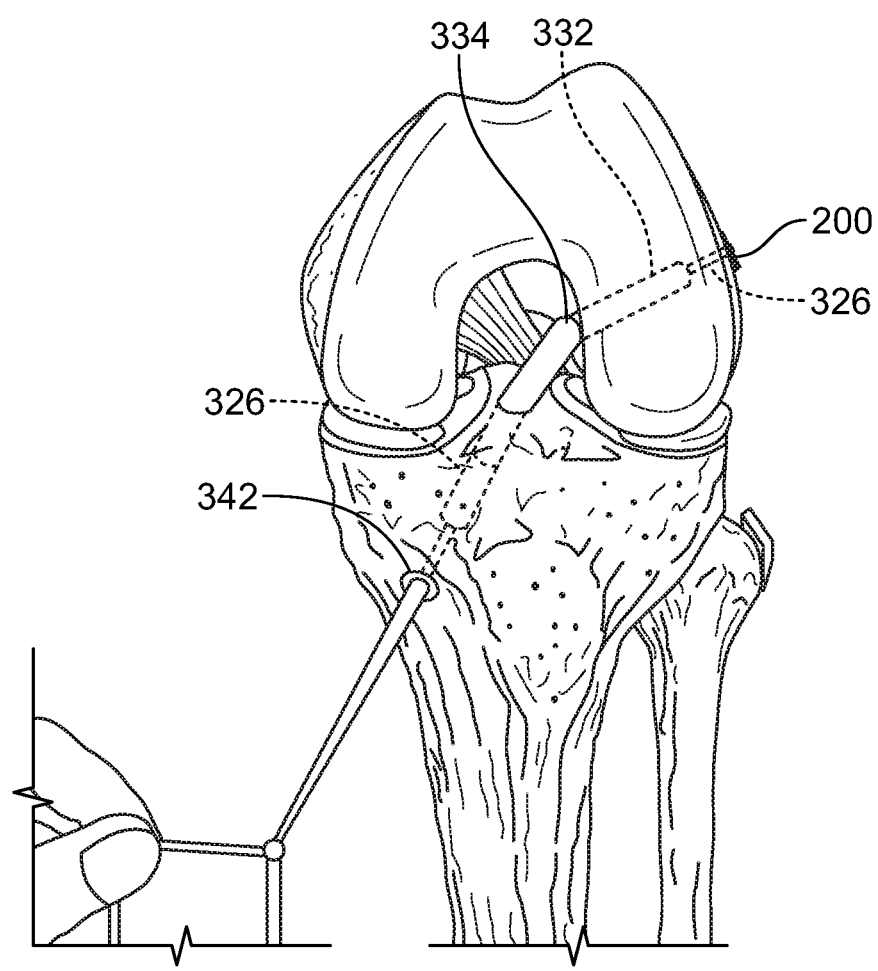
Figure 14:
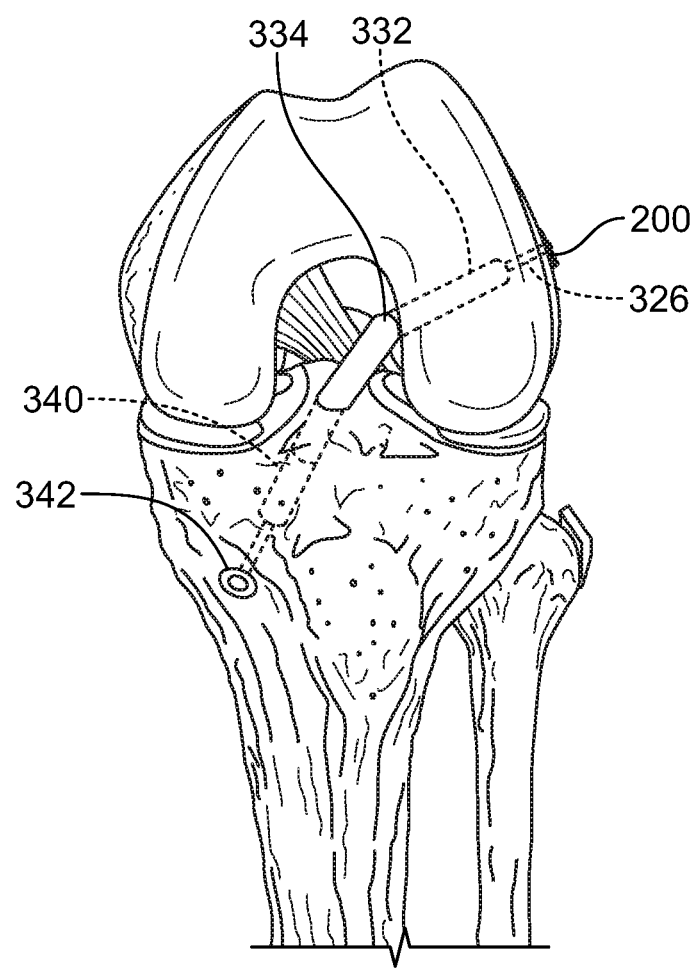

With reference to FIGS. 13-14, the method then involves, at block 312, fixating the tissue 334 to the socket 334 with the fixation button 200. In an example, this involves positioning the fixation button 200 against the second surface 326, and then tensioning the tissue 334 so that the fixation button 200 is tightly secured to the second surface 326. In particular, in the example of FIGS. 13-14, the tissue 334 is first positioned in tissue socket 332 by moving the eyelet 110 through the tissue socket 332 and tunnel 326. After the tissue 334 is positioned in tunnel socket 334, the tissue 334 is then positioned in tibial socket 340. Tibial socket can be formed in a similar manner as tissue socket 332. In another example, tibial socket 340 can be formed in another manner, such as with a retrograde reamer. The tissue 334 is then tensioned in the sockets 332 and 340, so that fixation button 200 and fixation button 342 are firmly secured to the bone.

Figure 15:
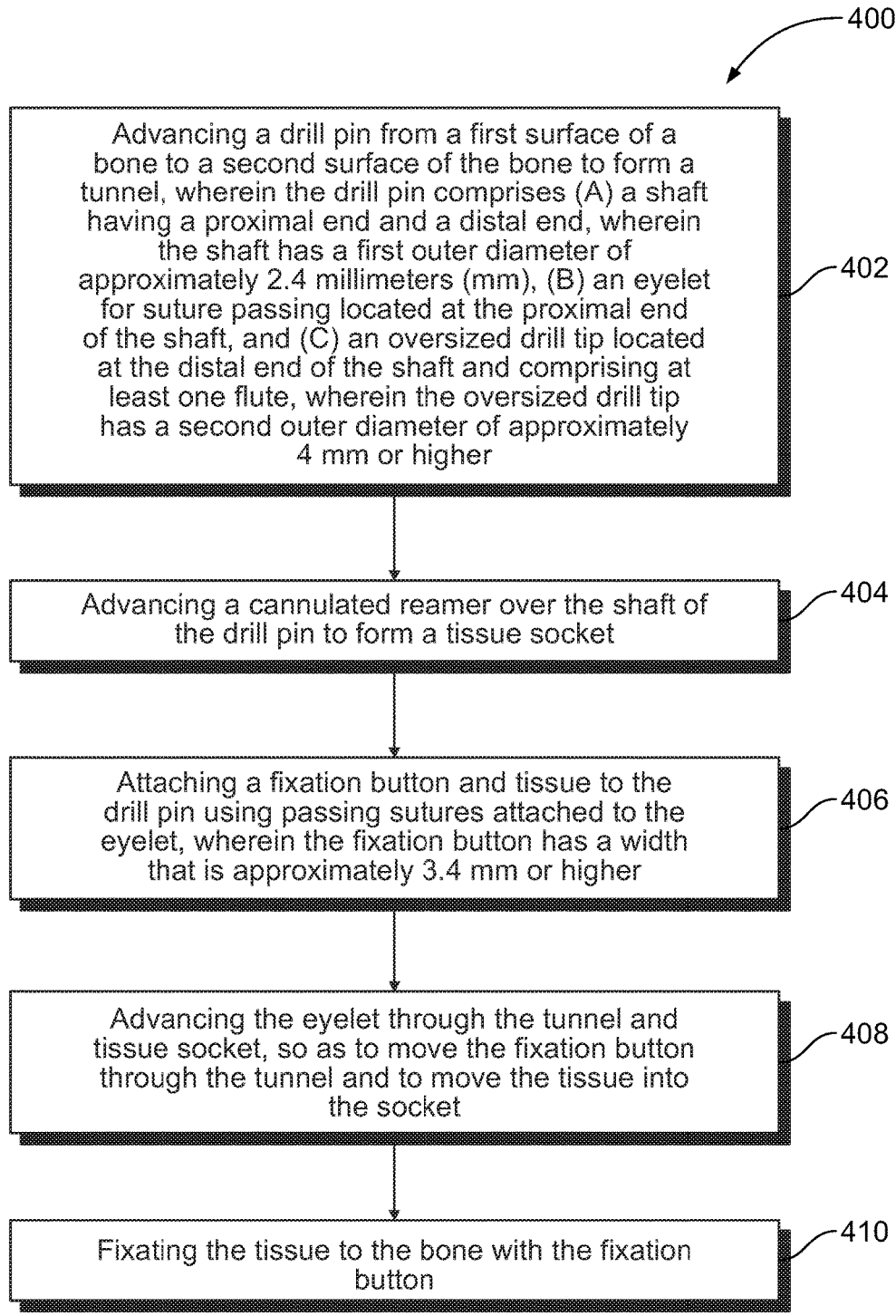
FIG. 15 shows a flowchart of an example method for fixating tissue to a bone with a fixation button, according to an example embodiment.

FIG. 15 is a flowchart of a second example method 400, in accordance with an embodiment. Note that example method 400 can be carried out by a drill pin such as drill pin 100; furthermore, example method 400 is related in some respects to method 300, and thus is not described in as great of detail. It should be explicitly noted, however, that any possibilities and permutations described above with respect to method 300 can equally apply to example method 400.

As shown in FIG. 15, example method 400 involves, at block 402, advancing a drill pin from a first surface of a bone to a second surface of the bone to form a tunnel. The drill pin comprises (a) a shaft having a proximal end and a distal end, wherein the shaft has a first outer diameter of approximately 2.4 mm, (b) an eyelet for suture passing located at the proximal end of the shaft, and (c) an oversized drill tip located at the distal end of the shaft and comprising at least one flute, wherein the oversized drill tip has a second outer diameter of approximately 4 mm or higher. Example method 400 then involves, at block 404, advancing a cannulated reamer over the shaft of the drill pin to form a tissue socket. Example method 400 also involves, at block 406, attaching a fixation button and tissue to the drill pin using passing sutures attached to the eyelet, wherein the fixation button has a width that is approximately 3.4 mm or higher. Further, method 400 involves, at block 408, advancing the eyelet through the tunnel and tissue socket, so as to move the fixation button through the tunnel and to move the tissue into the socket. Still further, method 400 involves, at block 410, fixating the tissue to the bone with the fixation button.

In an example embodiment of example method 400, the drill pin further includes markings along the shaft to allow measurement of a distance from the oversized drill tip, and the method 400 also involves positioning the oversized drill tip against the second surface of the bone and determining a depth of the tunnel based on the markings along the shaft.

The disclosed methods and systems for fixating tissue to a bone with a fixation button provide numerous advantages over existing systems and methods for fixating tissue to a bone with a fixation button. For example, existing guide pins for ligament repair and reconstruction operations form tunnels less than 4 mm in diameter and thus, it is necessary to over drill the guide pin in order to form a tunnel large enough to accommodate a fixation button. However, the disclosed methods and systems provide for the ability to install a fixation button having a 3.4 mm width or higher without over drilling the tunnel formed by the drill pin. By avoiding over drilling of the tunnel 326 formed by the drill pin, the overall operation time is beneficially reduced.

As another example, the disclosed methods and systems provide an improved way to measure tunnel depth that is more efficient and more precise than existing methods. As mentioned above, one existing method of measuring tunnel depth involves removing the drill pin and using a measurement instrument separate from the drill pin to measure tunnel depth. However, this method involves an additional tool and step to perform the measurement which increases the time and complexity of the operation. In contrast, the disclosed methods and systems do not involve using an additional measurement tool and thus can help to reduce the time of operation. Further, as mentioned above, existing drill pins can include markings along the longitudinal axis of the drill pin. Although existing drill pins can include laser markings along the longitudinal axis of the drill pin, existing drill pins do not include an oversized drill tip that can reliably be used as a positive stop against the bone. Thus, the disclosed systems and method beneficially provide improved methods and system to measure the tunnel depth. This improved way to measure tunnel depth can help to obtain a more precise measurement of tunnel depth. Further, this improved way to measure tunnel depth can also allow a surgeon to more efficiently perform the measurement, which can help to decrease the operation time.

Further, the disclosed oversized drill tip allows for providing a tip that is configured to drill a 4 mm or larger tunnel while still maintaining a 2.4 mm flexible shaft. By maintaining a 2.4 mm flexible shaft, the disclosed drill pin 100 can be used with existing cannulated reamers to form the tunnel socket 326. Some existing drill pins include a 2.4 mm shaft and drill tip somewhat larger than 2.4 mm. For instance, some existing drill pins include spade tips that are larger than 2.4 mm. However, spade tips substantially larger than 2.4 mm that are attached to a 2.4 mm flexible shaft are not compatible with a curved guide, as the flat spade tip does not spin inside the cannulation of the device as well as the disclosed oversized, substantially cylindrical, and fluted drill tip. Therefore, the disclosed oversized, substantially cylindrical, and fluted drill tip offers advantages over existing drill pins having spade tips.

An example curved guide is described with reference to FIGS. 16A-B and 17. In particular, FIG. 16A illustrates an example curved guide 500 that can be used with a drill pin such as drill pin 100 during an example embodiment of the drilling process. The curved guide 500 includes a curved, cannulated tube 502 in which the drill pin 100 can be inserted. A distal end 504 of the cannulated tube 502 includes a recessed portion 506. In an example embodiment, during use, the oversized drill tip 112 sits in the recessed portion 506 at the distal end 504 of the curved guide 500 (see FIG. 17). The oversized drill tip 112 can spin within this recessed portion 506. Although a curved guide is depicted in FIGS. 16A-B, in other embodiments non-curved guides can also be used with the drill pin 100. For instance, in another example embodiment, a guide having a straight cannulated tube may be used with the drill pin 100 during an operation.

Throughout this description, the term "approximately" refers to a recited parameter or value that need not be achieved exactly, but that deviations or variations, including for example, tolerances, manufacturing tolerances, measurement error, measurement accuracy limitations and other factors known to skill in the art, may occur in amounts that do not preclude the effect the parameter or value was intended to provide. For instance, as used herein, "approximately X mm" means any distance in the range of X mm+/−0.01*(X mm). Further, as used herein, "approximately X degrees" means any degree in the range of X degrees+/−0.1*(X degrees).

Further, the term "substantially" refers to a recited characteristic that need not be achieved exactly, but that deviations or variations, including for example, tolerances, measurement error, measurement accuracy limitations and other factors known to skill in the art, may occur in amounts that do not preclude the effect the characteristic was intended to provide.

Still further, although the disclosed systems and methods are described with reference to fixating tissue to a bone with a fixation button during ACL and/or PCL reconstruction operations, it should be understood that disclosed systems and methods can be implemented during other procedures as well, including but not limited to operations for knee collateral ligament operations, biceps tendon operations, anterior talofibular ligament (ATFL) operations, and acromioclavicular (AC) joint operations. The disclosed systems and methods can be used in any operation involving fixating bone and/or tissue to a bone with a fixation button.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A method of fixating tissue to a bone with a fixation button, the method comprising:
   (i) advancing a drill pin from a first surface of a bone to a second surface of the bone to form a tunnel, wherein the drill pin comprises (a) a flexible shaft having a first outer diameter, (b) an eyelet for suture passing located on the flexible shaft, (c) an oversized drill tip located at a distal end of the flexible shaft and comprising at least one flute, wherein the oversized drill tip has a second outer diameter that is at least 1.5 times the first outer diameter, and (d) markings along the flexible shaft to allow measurement of a distance from the oversized drill tip;
   (ii) positioning the oversized drill tip against the second surface of the bone and determining a depth of the tunnel based on the markings along the flexible shaft;
   (iii) advancing a cannulated reamer over the flexible shaft of the drill pin to form a tissue socket having a diameter greater than the second outer diameter and a length less than the determined tunnel depth;
   (iv) attaching a fixation button and tissue to the drill pin using passing sutures attached to the eyelet, wherein the fixation button has a width that is greater than the first outer diameter of the flexible shaft but less than the second outer diameter of the oversized drill tip;
   (v) advancing the eyelet through the tunnel and tissue socket, so as to move the fixation button through the tunnel and to move the tissue into the socket; and
   (vi) fixating the tissue to the socket with the fixation button.

2. The method of claim 1, wherein the first outer diameter is approximately 2.4 mm, wherein the second outer diameter is approximately 4 mm or higher, and wherein the width is approximately 3.4 mm or higher.

3. The method of claim 1, wherein the flexible shaft and oversized drill tip comprise nitinol.

4. The method of claim 1, wherein the oversized drill tip is a substantially cylindrical drill tip comprising a cutting edge having three flats spaced approximately 120 degrees apart.

5. The method of claim 1, wherein the flexible shaft comprises a longitudinal axis,
   wherein a proximal end of the oversized drill tip comprises a proximal surface that is substantially perpendicular to the longitudinal axis of the flexible shaft, and
   wherein positioning the oversized drill tip against the second surface of the bone comprises positioning the substantially-perpendicular proximal surface against the second surface of the bone.

6. The method of claim 5, wherein the proximal surface that is substantially perpendicular to the longitudinal axis of the flexible shaft extends at an angle between 75 and 105 degrees from the longitudinal axis of the flexible shaft.

7. The method of claim 1, wherein attaching a fixation button and tissue to the drill pin using passing sutures attached to the eyelet comprises:
   attaching the fixation button and the tissue;
   attaching the passing sutures to the fixation button; and
   after attaching the passing sutures to the fixation button, securing the passing sutures to the eyelet.

8. The method of claim 1, wherein the drill pin is an un-cannulated drill pin.

9. The method of claim 1, wherein the eyelet is a slot formed integral with the flexible shaft.

10. The method of claim 1, wherein the tissue comprises a ligament or a tendon.

11. A method of fixating a tissue to a bone with a fixation button, the method comprising:
   (i) advancing a drill pin from a first surface of a bone to a second surface of the bone to form a tunnel, wherein the drill pin comprises (a) a shaft having a proximal end and a distal end, wherein the shaft has a first outer diameter of approximately 2.4 mm, (b) an eyelet for suture passing located at the proximal end of the shaft, and (c) an oversized drill tip located at the distal end of the shaft and comprising at least one flute, wherein the oversized drill tip has a second outer diameter of approximately 4 mm or higher;
   (ii) advancing a cannulated reamer over the shaft of the drill pin to form a tissue socket;
   (iii) attaching a fixation button and tissue to the drill pin using passing sutures attached to the eyelet, wherein the fixation button has a width that is approximately 3.4 mm or higher;
   (iv) advancing the eyelet through the tunnel and tissue socket, so as to move the fixation button through the tunnel and to move the tissue into the socket; and
   (v) fixating the tissue to the bone with the fixation button.

12. The method of claim 11, wherein the drill pin further comprises markings along the shaft to allow measurement of a distance from the oversized drill tip, and wherein the method further comprises:

positioning the oversized drill tip against the second surface of the bone and determining a depth of the tunnel based on the markings along the shaft.

13. The method of claim 12, wherein the shaft comprises a longitudinal axis, wherein a proximal end of the oversized drill tip comprises a proximal surface that is substantially perpendicular to the longitudinal axis of the shaft, and wherein positioning the oversized drill tip against the second surface of the bone comprises positioning the substantially-perpendicular proximal surface against the second surface of the bone.

14. The method of claim 11, wherein the shaft and oversized drill tip comprise nitinol.

15. The method of claim 11, wherein the shaft is formed from a stainless steel or stainless steel tubing.

16. The method of claim 11, wherein the oversized drill tip is formed from a stainless steel or stainless steel tubing.

17. The method of claim 11, wherein the oversized drill tip is a substantially cylindrical drill tip comprising a cutting edge having three flats spaced approximately 120 degrees apart.

18. The method of claim 17, wherein the proximal surface that is substantially perpendicular to the longitudinal axis of the shaft extends at an angle between 75 and 105 degrees from the longitudinal axis of the shaft.

19. The method of claim 11, wherein the drill pin is an un-cannulated drill pin.

20. The method of claim 11, wherein the eyelet comprises a wire loop crimped to a proximal end of the shaft or a slot formed integral with the shaft.

21. A method of fixating tissue to a bone with a fixation button, the method comprising:

(i) advancing a drill pin from a first surface of a bone to a second surface of the bone to form a tunnel, wherein the drill pin comprises (a) a flexible shaft having a first outer diameter, (b) an eyelet for suture passing located on the flexible shaft, (c) an oversized drill tip located at a distal end of the flexible shaft and comprising at least one flute, wherein the oversized drill tip has a second outer diameter that is at least about 1.25 to about 1.75 times the first outer diameter, and (d) markings along the flexible shaft to allow measurement of a distance from the oversized drill tip;

(ii) positioning the oversized drill tip against the second surface of the bone and determining a depth of the tunnel based on the markings along the flexible shaft;

(iii) advancing a cannulated reamer over the flexible shaft of the drill pin to form a tissue socket having a diameter greater than the second outer diameter and a length less than the determined tunnel depth;

(iv) attaching a fixation button and tissue to the drill pin using passing sutures attached to the eyelet, wherein the fixation button has a width that is greater than the first outer diameter of the flexible shaft but less than the second outer diameter of the oversized drill tip;

(v) advancing the eyelet through the tunnel and tissue socket, so as to move the fixation button through the tunnel and to move the tissue into the socket; and (vi) fixating the tissue to the socket with the fixation button.

* * * * *